US00PP26406P2

(12) United States Plant Patent
Lannes

(10) Patent No.: US PP26,406 P2
(45) Date of Patent: Feb. 9, 2016

(54) ***MANDEVILLA* PLANT NAMED 'LANSOUTHCAROLINA'**

(50) Latin Name: *Mandevilla hybrida*
Varietal Denomination: Lansouthcarolina

(71) Applicant: Robert Lannes, Malause (FR)

(72) Inventor: Robert Lannes, Malause (FR)

(73) Assignee: D. H. M. Innovation S.A.S., Malause (FR)

( * ) Notice: Subject to any disclaimer, the term of this patent is extended or adjusted under 35 U.S.C. 154(b) by 73 days.

(21) Appl. No.: 13/998,545

(22) Filed: Nov. 8, 2013

(51) Int. Cl.
*A01H 5/02* (2006.01)

(52) U.S. Cl.
USPC ..... Plt./232

(58) Field of Classification Search
USPC ..... Plt./232
CPC ..... A01H 5/02; A01H 5/00
See application file for complete search history.

(56) References Cited

PUBLICATIONS http://www.hydrotip.de/mandevilla-• -amabilis-backh-backh-f-dress-lansouthcarolina_pic_11779.html; (Translated), Jan. 23, 2013.*
http://www.hydrotip.de/ipm-essen-2013_rubrik_602.html; (Translated), Jan. 23, 2013.*

* cited by examiner

*Primary Examiner* — Kent L Bell
(74) *Attorney, Agent, or Firm* — C. A. Whealy

(57) ABSTRACT

A new and distinct cultivar of *Mandevilla* plant named 'Lansouthcarolina', characterized by its upright plant habit; moderately vigorous growth habit; freely branching habit; dark green-colored leaves; freely flowering habit; and large pink-colored flowers.

2 Drawing Sheets

Botanical designation: *Mandevilla hybrida.*
Cultivar denomination: 'LANSOUTHCAROLINA'.

BACKGROUND OF THE INVENTION

The present invention relates to a new and distinct cultivar of *Mandevilla* plant, botanically known as *Mandevilla hybrida* and hereinafter referred to by the name 'Lansouthcarolina'.

The new *Mandevilla* plant is a product of a planned breeding program conducted by the Inventor in Malause, France. The objective of the breeding program is to create new upright *Mandevilla* plants with large leaves and flowers.

The new *Mandevilla* plant originated from a cross-pollination conducted by the Inventor in Malause, France in June, 2009 of *Mandevilla hybrida* 'Sunmandeho', disclosed in U.S. Plant Pat. No. 11,556, as the female, or seed parent with a proprietary selection of *Mandevilla hybrida* identified as code number 06-812-02, not patented, as the male, or pollen, parent. The new *Mandevilla* plant was discovered and selected by the Inventor as a single flowering plant from within the progeny of the stated cross-pollination in a controlled greenhouse environment in Malause, France in June, 2012.

Asexual reproduction of the new *Mandevilla* plant by cuttings in a controlled greenhouse environment in Malause, France, since December, 2012 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices.

The phenotype may vary somewhat with variations in environmental conditions such as temperature and light intensity without, however, any variance in genotype.

The following traits have been repeatedly observed and are determined to be the unique characteristics of 'Lansouthcarolina'. These characteristics in combination distinguish 'Lansouthcarolina' as a new and distinct *Mandevilla* plant:

1. Upright plant habit.
2. Moderately vigorous growth habit.
3. Freely branching habit.
4. Dark green-colored leaves.
5. Freely flowering habit.
6. Large pink-colored flowers.

Plants of the new *Mandevilla* can be compared to plants of the female parent, 'Sunmandeho'. Plants of the new *Mandevilla* differ primarily from plants of 'Sunmandeho' in the following characteristics:

1. Plants of the new *Mandevilla* are more upright than and not as vining as plants of 'Sunmandeho'.
2. Plants of the new *Mandevilla* have shorter internodes than plants of 'Sunmandeho'.
3. Plants of the new *Mandevilla* and 'Sunmandeho' differ in flower color as plants of 'Sunmandeho' have yellowish white-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* have larger leaves than plants of the male parent selection.
2. Plants of the new *Mandevilla* have larger flowers than plants of the male parent selection.

3. Plants of the new *Mandevilla* and the male parent selection differ in flower shape and color as plants of the male parent selection have rounded red-colored flowers.

Plants of the new *Mandevilla* can also be compared to plants of *Mandevilla sanderi* 'Lanarizona', disclosed in U.S. Plant Pat. No. 23,672. In side-by-side comparisons conducted in Malause, France, plants of the new *Mandevilla* differed primarily from plants of 'Lanarizona' in flower color as plants of 'Lanarizona' have white-colored flowers. In addition, plants of the new *Mandevilla* had shorter internodes and were more upright than and not as vining as plants of 'Lanarizona'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lansouthcarolina' grown in a container.

The photograph on the second sheet is a close-up view of typical flower buds and open flowers of 'Lansouthcarolina'.

DETAILED BOTANICAL DESCRIPTION

The aforementioned photographs and following observations, measurements and values describe plants grown during the spring in two-liter containers in polyethylene-covered greenhouse in Malause, France and under cultural practices typical of *Mandevilla* commercial production. During the production of the plants, day temperatures ranged from 15° C. to 26° C. and night temperatures ranged from 14° C. to 15° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla hybrida* 'Lansouthcarolina'.

Parentage:

*Female, or seed, parent.*—*Mandevilla hybrida* 'Sunmandeho', disclosed in U.S. Plant Pat. No. 11,556.

*Male, or pollen, parent.*—Proprietary selection of *Mandevilla hybrida* identified as code number 06-812-02, not patented.

Propagation:

*Type.*—By vegetative cuttings.

*Time to initiate roots, summer.*—About two weeks at 23° C. to 30° C.

*Time to initiate roots, winter.*—About three weeks at 23° C. to 25° C.

*Time to produce a rooted young plant, summer.*—About five to six weeks at 23° C. to 30° C.

*Time to produce a rooted young plant, winter.*—About six to eight weeks at 23° C. to 25° C.

*Root description.*—Fibrous, fine; light yellowish white in color.

*Rooting habit.*—Freely branching; medium density.

Plant description:

*Plant and growth habit.*—Upright plant habit; moderately vigorous growth habit.

*Plant height.*—About 43 cm.

*Plant diameter (spread).*—About 46.3 cm.

*Lateral branch description.*—Branching habit: Freely branching habit with about nine lateral branches developing per plant; pinching enhances lateral branch development. Length: About 18.9 cm. Diameter: About 4 mm. Internode length: About 4.3 cm. Strength: Strong. Texture: Densely pubescent. Color, developing: Close to 145A. Color, developed: Close to 199A to 199B.

Leaf description:

*Arrangement.*—Opposite, simple.

*Length.*—About 9.1 cm.

*Width.*—About 4.3 cm.

*Shape.*—Oblong to narrowly elliptic or ovate.

*Apex.*—Apiculate.

*Base.*—Truncate.

*Margin.*—Entire, undulate.

*Texture, upper and lower surfaces.*—Densely pubescent.

*Venation pattern.*—Pinnate, reticulate.

*Color.*—Developing leaves, upper surface: Close to between 143A and 144A. Developing leaves, lower surface: Close to 144A. Full expanded leaves, upper surface: Close to between N137A and 139A; venation, close to 144A. Fully expanded leaves, lower surface: Close to 146B; venation, close to 144C.

*Petiole length.*—About 1 cm.

*Petiole diameter.*—About 2 mm.

*Petiole texture, upper and lower surfaces.*—Smooth, glabrous.

*Petiole color, upper and lower surfaces.*—Close to 144B to 144C.

Flower description:

*Flower type and flowering habit.*—Single salverform flowers arranged in axillary cymes; flowers star-shaped and face mostly outwardly; freely flowering habit with about eleven flowers developing per inflorescence and about 250 flowers developing per plant.

*Natural flowering season.*—Plants flower continuously from early summer into the autumn in France.

*Flower longevity on the plant.*—About seven days; flowers not persistent.

*Fragrance.*—Faint; sweet and pleasant.

*Inflorescence height.*—About 21 cm.

*Inflorescence diameter.*—About 14.1 cm.

*Flower buds.*—Length: About 6.2 cm. Diameter: About 1 cm. Shape: Narrowly elliptic. Color: Close to 157C to 157D; towards the base and apex, close to 145C to 145D.

*Flowers.*—Appearance: Flared trumpet, corolla fused and five-parted. Diameter: About 8.9 cm. Depth (length): About 6.7 cm. Tube length: About 4.3 cm.

*Corolla.*—Quantity and arrangement: Five petals arranged in a single whorl and fused toward the base. Petal length: About 8.3 cm. Petal width: About 3.8 cm. Petal shape and appearance: Roughly spatulate; lower 52% of the petal is fused. Petal apex: Non-symmetrically acute. Petal margin: Entire. Petal texture, upper and lower surfaces: Smooth, glabrous; moderately velvety. Throat and tube texture: Smooth, glabrous. Color: Petal, when opening and fully opened, upper surface: Close to 65B flushed with close to 65C to 65D; color becoming closer to 65A with development; towards the throat, close to 64D and 31A; throat, close to 11B; base of the throat, close to 145A to 145B. Petal, when opening and fully opened, lower surface: Close to 65C to 65D; tube distally, slightly darker than 65B; tube, close to 145B.

*Corona*.—Quantity and arrangement: Five sepals arranged in a single whorl. Sepal length: About 6 mm. Sepal width: About 2 mm. Sepal shape: Lanceolate. Sepal apex: Narrowly acuminate. Sepal base: Roughly truncate. Sepal margin: Entire. Sepal texture, upper and lower surfaces: Smooth, glabrous. Sepal color: Immature, upper and lower surfaces: Close to 145A, apices, close to 46A. Mature, upper and lower surfaces: Close to 145B; apices, close to 46A.

*Peduncles*.—Length: About 17.4 cm. Diameter: About 3 mm. Texture: Smooth, glabrous. Strength: Flexible, but strong. Color: Close to 143B.

*Pedicels*.—Length: About 2.3 cm. Diameter: About 2 mm. Texture: Smooth, glabrous. Strength: Flexible, but strong. Color: Close to 145A.

*Reproductive organs*.—Stamens: Quantity and arrangement: Typically five; basifixed; anthers connivent. Filament length: About 1 mm. Anther shape: Narrowly oblong. Anther length: About 8 mm. Anther color: Close to 161C to 161D. Pollen amount: None observed. Pistils: Quantity: Typically one. Pistil length: About 2 cm. Style length: About 1.8 cm. Style color: Close to 145C. Stigma shape: Sagittate. Stigma color: Close to 144C. Ovary color: Close to 144B.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'Lansouth-carolina' as illustrated and described.

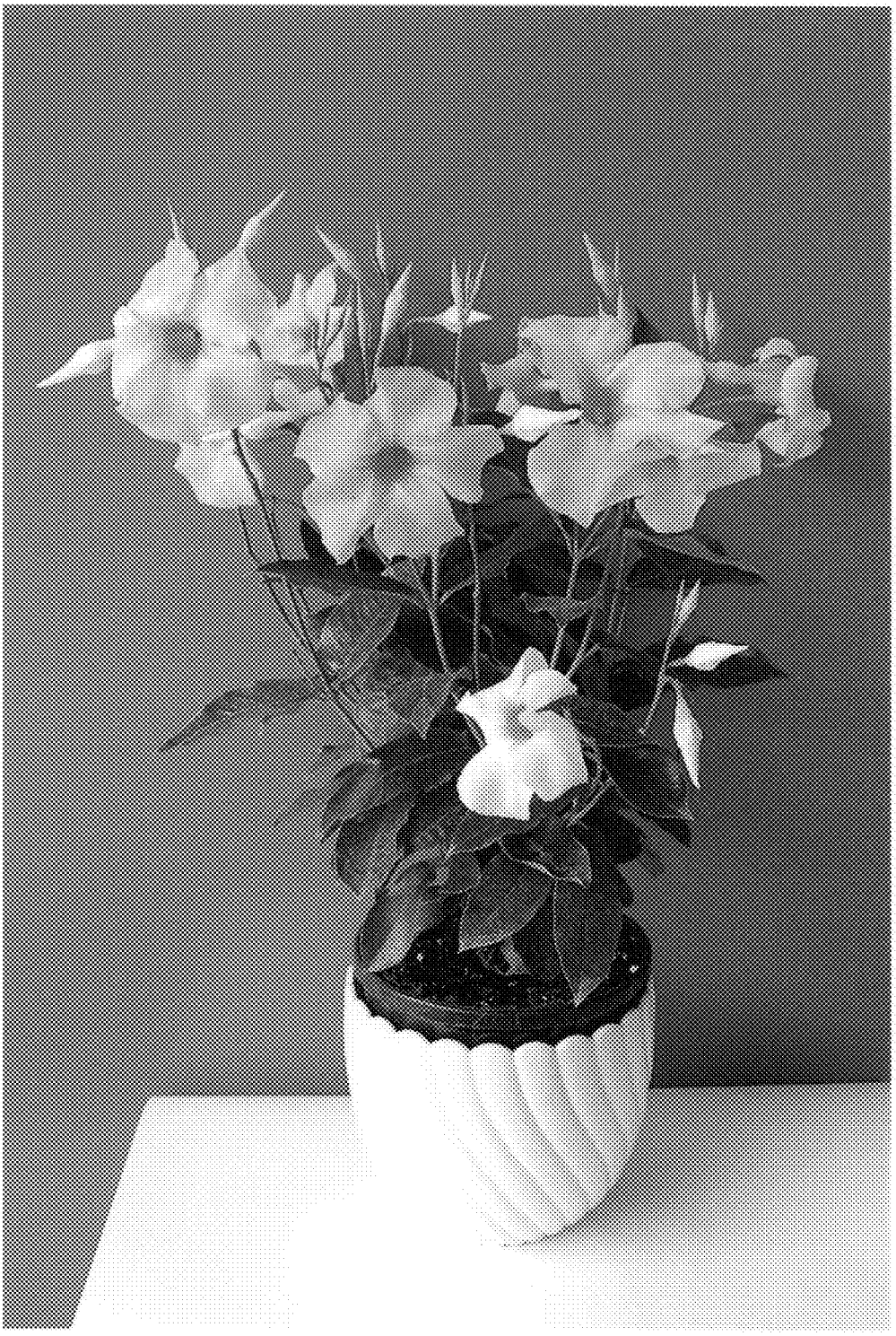

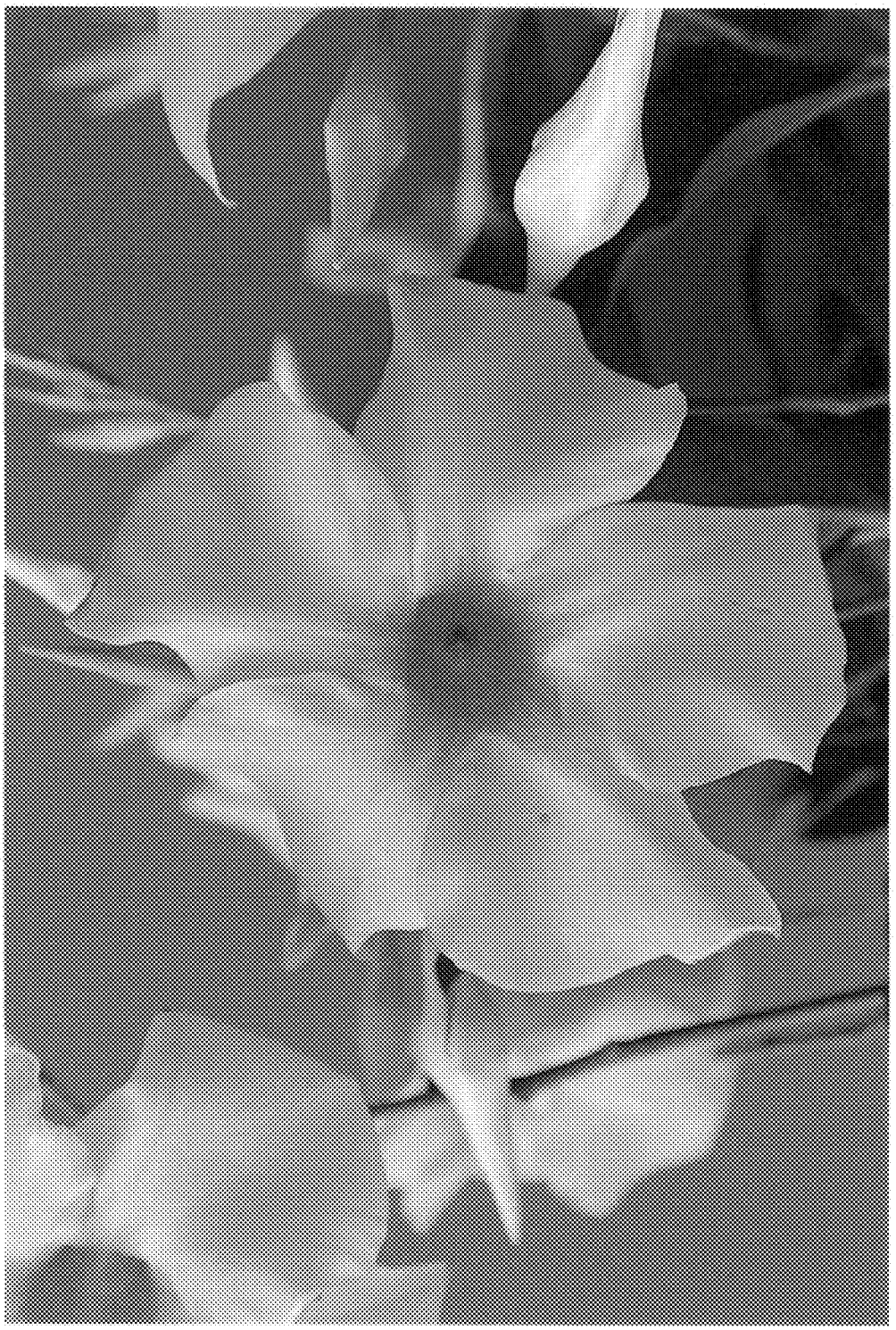

* * * * *